United States Patent
Newmark et al.

(10) Patent No.: US 7,070,816 B2
(45) Date of Patent: *Jul. 4, 2006

(54) METHODS FOR TREATING PROSTATIC INTRAEPITHELIAL NEOPLASIA WITH HERBAL COMPOSITIONS

(75) Inventors: Thomas Newmark, St. Louis, MO (US); Paul Schulick, Brattleboro, VT (US); Aaron Katz, New York, NY (US)

(73) Assignee: New Chapter, Inc., Brattleboro, VT (US)

( * ) Notice: Subject to any disclaimer, the term of this patent is extended or adjusted under 35 U.S.C. 154(b) by 261 days.

This patent is subject to a terminal disclaimer.

(21) Appl. No.: 10/728,085

(22) Filed: Dec. 5, 2003

(65) Prior Publication Data

US 2005/0123630 A1 Jun. 9, 2005

(51) Int. Cl.
*A01N 65/00* (2006.01)

(52) U.S. Cl. .................. 424/725; 424/729; 424/745; 424/756

(58) Field of Classification Search ................. None
See application file for complete search history.

(56) References Cited

U.S. PATENT DOCUMENTS

| | | | |
|---|---|---|---|
| 5,344,991 A | 9/1994 | Reitz et al. | |
| 5,380,738 A | 1/1995 | Norman et al. | |
| 5,393,790 A | 2/1995 | Reitz et al. | |
| 5,434,178 A | 7/1995 | Talley et al. | |
| 5,474,995 A | 12/1995 | Ducharme et al. | |
| 5,510,368 A | 4/1996 | Lau et al. | |
| 5,935,860 A | 8/1999 | Patierno et al. | |
| 6,261,607 B1 * | 7/2001 | Newmark et al. | ........... 424/727 |
| 6,265,448 B1 | 7/2001 | Steiner et al. | |
| 6,387,416 B1 * | 5/2002 | Newmark et al. | ........... 424/725 |
| 6,410,043 B1 | 6/2002 | Steiner et al. | |
| 6,413,533 B1 | 7/2002 | Steiner et al. | |
| 6,413,534 B1 | 7/2002 | Steiner et al. | |
| 6,413,535 B1 | 7/2002 | Steiner et al. | |
| 6,477,426 B1 | 11/2002 | Fenn et al. | |
| 6,488,957 B1 * | 12/2002 | Koumarianos | ............... 424/439 |
| 6,541,045 B1 * | 4/2003 | Charters et al. | ............ 424/737 |
| 6,630,301 B1 | 10/2003 | Gocke et al. | |
| 6,632,447 B1 | 10/2003 | Steiner et al. | |

FOREIGN PATENT DOCUMENTS

| | | |
|---|---|---|
| WO | WO 94/13635 | 6/1994 |
| WO | WO 94/15932 | 7/1994 |
| WO | WO 94/20480 | 9/1994 |
| WO | WO 94/26731 | 11/1994 |
| WO | WO 94/27980 | 12/1994 |
| WO | WO 95/00501 | 1/1995 |
| WO | WO 95/15316 | 6/1995 |
| WO | WO 96/03387 | 2/1996 |
| WO | WO 96/03388 | 2/1996 |
| WO | WO 96/06840 | 3/1996 |
| WO | WO 96/25405 | 8/1996 |

OTHER PUBLICATIONS

Chandrasekharan, N.V. et al. "COX-3, a cyclooxygenase-1 variant inhibited by acetaminophen and other analgesic/antipyretic drugs: Cloning, structure, and expression", *PNAS*, vol. 99 (21), pp. 13926-13931, 2002.

Alsikafi, N.F. et al. "High-grade prostatic intraepithelial neoplasia with adjacent atypia is associated with a higher incidence of cancer on subsequent needle biopsy than high-grade prostatic intrepithelial neoplasia along", *Urology*, vol. 57 (2) pp. 296-300, 2001.

* cited by examiner

*Primary Examiner*—Christopher R. Tate
(74) *Attorney, Agent, or Firm*—Nath & Associates PLLC; Gary M. Nath; Jerald L. Meyer

(57) ABSTRACT

The inventive subject matter relates to methods for treating prostatic intraepithelial neoplasia, comprising administration of a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis,* rosemary, green tea, huzhang, Chinese goldthread, and barberry.

43 Claims, No Drawings

METHODS FOR TREATING PROSTATIC INTRAEPITHELIAL NEOPLASIA WITH HERBAL COMPOSITIONS

BACKGROUND OF THE INVENTIVE SUBJECT MATTER

1. Field of the Inventive Subject Matter

The present inventive subject matter relates to novel methods for treating prostatic intraepithelial neoplasia, comprising administration of a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

2. Background

Prostatic Intraepithelial Neoplasia. About 200,000 American men are diagnosed with prostate cancer each year, and millions more develop undiagnosed or hidden microscopic cancer. About 80% of men have microscopic prostate cancer by age 80 years, and the autopsy frequency of prostate cancer is remarkably similar in men around the world despite large differences in clinical detection.

Prostatic intraepithelial neoplasia (hereinafter "PIN") refers to the putative precancerous end of the continuum of cellular proliferations within the lining of prostatic ducts, ductules, and acini. The term prostatic intraepithelial neoplasia has been generally accepted, although terms such as dysplasia, malignant transformation, and intraductal carcinoma have been used to describe the condition. PIN is characterized by cellular proliferations within pre-existing ducts and acini with cytologic changes mimicking cancer, including nuclear and nucleolar enlargement.

Physiological forms of PIN include tufting, micropapillary, cribriform, and flat. Tufting is the most common feature and is present in 97% of all PIN. Most histologic samples contain multiple patterns, and there are no prognostic differences among the various PIN patterns. PIN spreads through the prostatic ducts in 3 patterns similar to prostate cancer. In the first pattern, neoplastic cells replace the normal luminal secretory epithelium, but there is preservation of the basal layer and basement membrane. Foci of PIN may be indistinguishable from ductal spread of carcinoma when viewed by light microscopy. A second pattern is characterized by direct invasion through the ductal or acinar wall with disruption of the basal cell layer. In a third pattern, neoplastic cells invaginate between the basal cell layers, which sometimes has been described as pagetoid spread.

Prostatic intraepithelial neoplasia is generally accepted in the art as a likely pre-invasive stage of prostate adenocarcinoma. PIN has a high predictive value as a marker for adenocarcinoma, and its identification warrants repeat biopsy for concurrent or subsequent invasive carcinoma. Most studies suggest that a large majority of patients with PIN will develop carcinoma at some time. Some studies suggest that that about half to about two-thirds of patients diagnosed with PIN will develop carcinoma within only 2–3 years. Thus, there is a great need for an effective treatment for PIN as a means of reducing or preventing the development of prostate cancer.

The incidence and extent of PIN appear to increase with patient age. PIN is associated with progressive abnormalities of phenotype and genotype that are more similar to cancer than normal prostatic epithelium, indicating impairment of cell differentiation with advancing stages of prostatic carcinogenesis. The only generally utilized method for detection of PIN is biopsy; PIN does not significantly elevate serum PSA concentration or its derivatives, and it is not apparently visible by current imaging techniques. There is no accepted pharmaceutical or surgical standard of practice for treating PIN. Some studies suggest that androgen deprivation therapy decreases the prevalence and extent of PIN in some patients, suggesting that this form of treatment may be one possible method for chemoprevention. However, androgen deprivation therapy has several side effects, discussed in greater detail below, which make it a less than optimal treatment for many men.

PIN is the most significant risk factor for prostate cancer in needle biopsy specimens. Its role as the preinvasive stage of cancer has been confirmed in two separate mouse models (see Alsikafi, et al., *High-grade Prostatic Intraepithelial Neoplasia with Adjacent Atypia Is Associated with a Higher Incidence of Cancer on Subsequent Needle Biopsy than High-grade Prostatic Intraepithelial Neoplasia Alone*, Urology, 57(2):296–300 (2001); and Amin, et al., *Putative Precursor Lesions of Prostatic Adenocarcinoma: Fact or Fiction?* Mod. Pathol., 6(4):476–83 (1993)).

PIN coexists with cancer in more than 85% of cases, but retains an intact or fragmented basal cell layer, unlike cancer which lacks a basal cell layer. The clinical importance of recognizing PIN is based on its strong association with prostatic adenocarcinoma, and its identification in biopsy specimens of the prostate warrants further search for concurrent cancer. PIN alone has no apparent influence on serum Prostate Specific Antigen (hereinafter "PSA") concentration, and PSA levels are not correlated with PIN. If all procedures fail to identify coexistent carcinoma, and lacking a method for treating PIN, close surveillance and follow-up are indicated. Current clinical practices call for follow-up biopsy is suggested at three to six month intervals for two years, and thereafter at twelve-month intervals for life. Biopsies are both expensive and uncomfortable for the subject, and there is thus an unmet need for PIN treatments.

Although there is no accepted pharmaceutical or surgical standard of practice for treating PIN, to the extent they are used at all, current treatments for PIN include androgen deprivation therapy and radiation therapy. Androgen deprivation therapy has several possible complications, including problems with sexual function, osteoporosis, and loss of muscle mass. Radiation therapy has possible complications including loss of appetite, fatigue, skin reactions such as redness and irritation, rectal burning or injury, diarrhea, cystitis, and blood in the urine. Thus, there is a continuing need for alternative treatments for prostate cancer and for improved treatments for prostatic intraepithelial neoplasia.

Cyclooxygenase Inhibitors. Cyclooxygenase is an enzyme-protein complex with a variety of biochemical actions. There are at least three primary COX isoenzymes, COX-1, COX-2, and COX-3. COX-1 is a constitutive enzyme, produced at a reasonably consistent level at all times. It plays an important role in, for example, gastrointestinal protection, kidney function, and the aggregation of blood platelets. COX-2 production is not constant; it varies depending on signals from various biochemical catalysts. For example, in the case of arthritis inflammation and pain, COX-2 responds to tissue damage by oxidizing arachidonic acid, creating prostaglandins which in turn produce local inflammation. COX-3 has been identified relatively recently (Chandrasekharan, et al., PNAS U.S.A., 99(21):13926–31 (2002)). In humans, COX-3 mRNA is expressed most abundantly in the cerebral cortex and heart tissues. COX-3 activity is selectively inhibited by analgesic/antipyretic drugs. It has been suggested that inhibition of COX-3 could represent a mechanism by which these drugs decrease pain and possibly fever.

Prostaglandins play a major role in the inflammatory process and the inhibition of prostaglandin production, especially production of $PGG_2$, $PGH_2$, and $PGE_2$, has been a common target of anti-inflammatory drug discovery. However, common non-steroidal anti-inflammatory drugs (hereinafter "NSAIDs") that are active in reducing the prostaglandin-induced pain and swelling associated with the inflammation process are also active in affecting other prostaglandin-regulated processes not associated with the inflammation process.

NSAIDs have been found to prevent the production of prostaglandins by inhibiting enzymes in the human arachidonic acid/prostaglandin pathway, including the cyclooxygenase enzymes. Traditional non-steroidal anti-inflammatory drugs, such as aspirin, work by inhibiting both COX-1 and COX-2. Thus, non-specific NSAIDs can have a damaging effect on the gastrointestinal tract, kidneys, and liver; blocking COX-1 can make the stomach lining more vulnerable, and reduced thromboxane production thins the blood, making gastrointestinal hemorrhage more likely, and may cause inadequate regulation of cellular immune functions and the secretion of various cytokines. The use of high doses of most common NSAID's can produce severe side effects, including life threatening ulcers, that limit their therapeutic potential.

COX-2 is associated with inflammation and provides a viable target of inhibition which more effectively reduces inflammation and produces fewer and less drastic side effects. Thus, researchers have been motivated to develop selective COX-2 inhibitors to reduce inflammation and relieve pain without the gastrointestinal damage brought on by inhibiting COX-1. In addition, the current scientific understanding in the art suggests that COX-2 inhibition may serve an important function in promoting normal cell growth in the colon, pancreas, breast tissue, and other organ systems.

Some compounds which selectively inhibit cyclooxygenase-2 have been described in U.S. Pat. Nos. 5,380,738, 5,344,991, 5,393,790, 5,434,178, 5,474,995, 5,510,368 and WO documents WO96/06840, WO96/03388, WO96/03387, WO96/25405, WO95/15316, WO94/15932, WO94/27980, WO95/00501, WO94/13635, WO94/20480, and WO94/26731.

Drugs such as valdecoxib, celecoxib, and rofecoxib are intended to selectively inhibit COX-2 with minimal effect on COX-1. However, despite the emphasis on COX-2 inhibition, even these drugs appear to have serious long term side effects, such as the breakdown in digestive protective mucus and prevention of normal healing processes. Thus, there is also a continuing need for more specific and non-specific COX-2 inhibitors which avoid the side effects produced by current COX-1 and COX-2 inhibitors.

Natural COX-2 Inhibitors. Several herbs have been found to inhibit the COX-2 enzyme. For example, holy basil has been found to possess significant anti-inflammatory properties and is capable of blocking both the cyclooxygenase and lipoxygenase pathways of arachidonate metabolism. Ursolic acid and oleanolic acid, two of the recognized phytonutrients of holy basil, have been found to have a significant COX-2 inhibitory effect.

Similarly, shogaols and gingerols, pungent components of ginger, have been found to inhibit cyclooxygenase. Eugenol, another active constituent of several medical herbs, has also been found to be a 5-lipoxygenase inhibitor and to possess potent anti-inflammatory and/or anti-rheumatic properties.

*Scutellaria baicalensis* also has been found to inhibit the COX-2 enzyme. According to the USDA database, green tea contains six constituents having cyclooxygenase-inhibitor activity. According to the Napralert database, green tea contains fifty one constituents having anti-inflammatory activity. The polyphenols in green tea were found to cause a marked reduction in COX-2. Flavan-3-ol derivatives (+)-catechin, also present in green tea, have been reported to be COX-1 and COX-2 inhibitors. In addition, salicylic acid, another constituent of green tea, also has been found to be a COX-2 inhibitor.

Berberine, found in barberry and Chinese goldthread, has also been found to inhibit COX-2 without inhibiting COX-1 activity.

In U.S. Pat. No. 6,387,416, Applicants disclosed the inventive compositions and their use for reducing inflammation. The contents of U.S. Pat. No. 6,387,416 are hereby incorporated by reference in their entirety. Surprisingly, as discussed in greater detail below, it has been determined that the inventive compositions are useful for treating prostatic intraepithelial neoplasia as well.

Methods for Treating Prostatic Intraepithelial Neoplasia. We have found that COX-2 inhibitors are useful for treating some cancers. We have also found that COX-2 inhibitors are useful for treating prostatic intraepithelial neoplasia. Only a very few patents actually disclose the use of selective COX-2 inhibitors for treating cancer, and none disclose the use of specific or non-specific COX-2 inhibitors for treating prostatic intraepithelial neoplasia. The body of patent art related to PIN, relating to non-invasive diagnosis and methods of treatment using compounds which are not COX-2 inhibitors, is exemplified by the following U.S. Patents.

U.S. Pat. No. 5,935,860 to Patierno, et al., discloses a non-surgical method for identifying prostatic intraepithelial neoplasia, based on expression of the uteroglobin protein as a molecular marker for PIN.

U.S. Pat. Nos. 6,265,448, 6,410,043, 6,413,533, 6,413,534, 6,413,535, and 6,632,447 to Steiner, et al., disclose methods for chemoprevention of prostate neoplasias by administering to a subject an effective dose of specific disclosed chemopreventive agents to prevent recurrence of, suppress, or inhibit prostate cancer, benign prostatic hyperplasia, prostatic intraepithelial neoplasia, an abnormally high level of circulating prostate specific antibody (PSA).

U.S. Pat. No. 6,477,426 to Fenn, et al., discloses a system and method for safely heating and destroying cancerous and pre-cancerous conditions of the prostate, as well as benign and pre-benign lesions, including PIN, by irradiation of the prostate tissue with coherent or non-coherent phased array energy.

U.S. Pat. No. 6,630,301 to Gocke, et al., discloses detection of specific extracellular nucleic acids associated with neoplastic, pre-malignant, or proliferative disease, including PIN, in plasma or serum fractions of human or animal blood.

According to virtually all available evidence, PIN is a likely precursor of prostatic adenocarcinoma. The clinical importance of treating PIN is based on its strong association with prostatic adenocarcinoma. Based on the limited body of art disclosing the use of COX-2 inhibitors for treating cancer, the lack of any art relating to the use of COX-2 inhibitors for treating prostatic intraepithelial neoplasia, and the need for effective treatments for prostatic intraepithelial neoplasia as prostate cancer precursor in particular, it is apparent that there is a great and immediate need for methods for treating prostatic intraepithelial neoplasia with COX-2 inhibitors. This need is met by the inventive methods and compositions, which treat prostatic intraepithelial neoplasia and ultimately reduce or eliminate the incidence of prostate cancer, without significant short or long term side effects, such as the sexual dysfunction, androgen insufficiency effects, and gastrointestinal effects discussed above.

SUMMARY OF THE INVENTIVE SUBJECT MATTER

The present inventive subject matter relates to a method for treating prostatic intraepithelial neoplasia in a subject, comprising the step of administering an effective amount of a composition to said subject to treat or prevent said prostatic intraepithelial neoplasia, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis,* rosemary, green tea, huzhang, Chinese goldthread, and barberry.

The present inventive subject matter further is drawn to a method for precancerous cellular proliferations within prostatic ducts, ductiles and acini in a subject, comprising the step of administering an effective amount of a composition to said subject to treat or prevent said precancerous cellular proliferations, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis,* rosemary, green tea, huzhang, Chinese goldthread, and barberry.

DETAILED DESCRIPTION OF THE INVENTIVE SUBJECT MATTER

Definitions

The term "therapeutically effective amount" as used herein refers to that amount of the extract which will contribute to the prostatic intraepithelial neoplasia-treating ability of the composition.

The term "treating" as used herein refers to partial or total inhibition or prevention of the growth or spread of prostatic intraepithelial neoplasia, as well as partial or total destruction of cells having the neoplastic patterns of prostatic intraepithelial neoplasia.

The term "preventing" as used herein refers to either preventing the onset of prostatic intraepithelial neoplasia, or preventing the onset of a preclinically evident stage of prostatic intraepithelial neoplasia in individuals at risk. Also intended to be encompassed by this definition is the prevention of initiation for malignant cells, and the arrest or reversal of the progression of premalignant cells to malignant cells. This includes prophylactic treatment of those at risk of developing prostatic intraepithelial neoplasia. In other words, "preventing" also encompasses avoiding the progression of prostatic intraepithelial neoplasia into prostate cancer.

The term "supercritical gas" or "supercritical fluid" as used herein refers to a gas is that heated to a temperature critical point, over which the gas will maintain its gaseous state and not turn to a liquid regardless of pressure. A gas heated to a temperature above its critical point will become very dense on compression, so that its characterisitcs resmble those of a fluid, but will become liquid. Carbon dioxide is commonly used in applications requiring a supercritical fluid. The general properties of supercritical fluids and the general use of supercritical fluids in extraction processes are described in, e.g. Taylor, *Supercritical Fluid Extraction,* Wiley, 1996; McHugh and Krukonis, *Supercritical Fluid Extraction: Principles and Practice,* 2nd ed., Butterworth-Heinemann, 1994; and Williams and Clifford, *Supercritical Fluid Methods and Protocols,* Humana Press, 2000, the contents of which are incorporated by reference herein.

The term "supercritical extraction" as used herein refers to the technique in which hydrophobic compounds can be extracted from samples utilizing a supercritical fluid. The solvation power of a supercritical fluid is increased as the pressure and temperature are increased above their critical points, producing an effective solvent for the isolation of hydrophobic molecules.

The term "hydroalcoholic extraction" as used herein refers to to the technique in which hydrophillic compounds can be extracted from a sample utilizing a solution of alcohol and water, followed by evaporation of the solution to produce a extract consisting of dissolved solids.

The term "post-supercritical alcoholic extraction" as used herein refers to a combined extraction process utilizing both a supercritical extraction technique and a hydroalcoholic extraction technique.

The term "prostatic intraepithelial neoplasia" or "PIN" as used herein refers broadly to the condition of the prostate characterized by progressive abnormalities of phenotype and genotype which are intermediate between normal prostatic epithelium and cancer, indicating impairment of cell differentiation and regulatory control. PIN refers to the putative precancerous end of the continuum of cellular proliferations within the lining of prostatic ducts, ductules, and acini. It is characterized by cellular proliferations within pre-existing ducts and acini with cytologic changes mimicking cancer, with neoplastic patterns including nuclear and nucleolar enlargement, but without stromal invasion.

The term "subject" as used herein refers to any human or mammal subject who has prostatic intraepithelial neoplasia, preferably a human subject. For methods of prevention, the subject is any human or animal subject, preferably a human subject, who is at risk for developing an epithelial cell-derived prostatic intraepithelial neoplasia. The subject may be at risk due to exposure to carcinogenic agents, being genetically predisposed to have prostatic intraepithelial neoplasia, and the like.

The term "cyclooxygenase-2 inhibitor" or "COX-2 inhibitor" as used herein refers to a compound or composition which is able to inhibit cyclooxygenase-2 without adverse inhibition of cyclooxygenase-1.

Methods for Treating Prostatic Intraepithelial Neoplasia

Prostate cancer is one of the most common malignancies diagnosed in men and is the most common cancer found in men older than 60 years. A third of all men older than 50 years have a latent form of prostate cancer that may be activated into life-threatening prostate cancer. Prostatic intraepithelial neoplasia has been identified as a precursor lesion to prostatic carcinoma.

Prostatic intraepithelial neoplasia is generally accepted in the art as a likely pre-invasive stage of prostate adenocarcinoma. Most studies suggest that a large majority of patients with PIN will develop carcinoma at some time. Some studies suggest that that about half to about two-thirds of patients diagnosed with PIN will develop carcinoma within only 2–3 years. PIN is strongly predictive of adenocarcinoma, and it is expected that an effective treatment for PIN will reduce, delay, or eliminate later development of prostate adenocarcinoma. If cancer can be identified in an early or latent stage, we expect that the neoplastic process is reversible or more easily treatable. Thus, there is a great need for an effective treatment for PIN as a means of reducing the incidence or preventing the development of prostate cancer, a need whihc is met by administration of the inventive compositions.

Associated with the progression of PIN to cancer is an increase in angiogenesis, with an increase in the number of microvessels. The microvessels in PIN are shorter than those in benign epithelium, and they have irregular contours and open lumens, an increased number of endothelial cells, and a greater distance from the basement membrane. Without being bound by any particular theory of mode of action, we expect that the anti-angiogenesis properties of the inventive compositions will, at least in part, produce a reduction or elimination of PIN cells in a subject, and thus effectively treat PIN.

To the extent they are used at all, current treatments for PIN include androgen deprivation therapy and radiation therapy. Androgen deprivation therapy has several possible complications, including problems with sexual function, osteoporosis, and loss of muscle mass. Radiation therapy has possible complications including loss of appetite, fatigue, skin reactions such as redness and irritation, rectal burning or injury, diarrhea, cystitis, and blood in the urine. Thus, there is a significant need for effective treatments for prostatic intraepithelial neoplasia which do not produce the significant, and often severe, side effects of the prior art treatments.

The three main isoforms of cycloxygenase are COX-1, COX-2, and COX-3, and these enzymes are responsible for the production of the group of eicosanoids, prostaglandins. The COX-1 isoform has many important housekeeping functions in the cell, and is therefore constitutively produced throughout the body. COX-2, however, is usually absent until induced by specific stimuli. It is therefore not surprising that COX-2 is implicated in the progression of many disease states, including cancer. COX-2 has been found to be present in elevated levels in a variety of cancers, including lung, breast, colon, pancreatic, head and neck, skin, glioblastoma, and prostate cancer. As discussed above, COX-3 has only been relatively recently identified, and its relationship to cancer, if any, has not yet been determined.

Regarding prostatic intraepithelial neoplasia, it has been demonstrated that elevated levels of COX-2 are present in some tumor samples, and there is an increased level of COX-2 enzyme expression with disease progression. COX-2 activity and resultant prostaglandin production is also involved in tumor-induced angiogenesis, which we expect to be mediated by certain COX-2 inhibitors. Additionally, we expect that certain COX-2 inhibitors produce a re-initiation of apoptosis pathways, overcoming the anti-apoptotic factors secreted by pre-cancerous prostatic intraepithelial neoplasia cells, and leading to cell death.

Applicants have developed a mixture comprised of herbal extracts, and the mixture has COX-2 inhibitory activity. Applicants' compositions are unique in the herbs selected, in the combinations and ratios thereof, in the synergies and activities amongst the herbs, and in that they are prepared via a supercritical $CO_2$ extraction process. Unlike traditional solvent based extraction methods, supercritical $CO_2$ extraction allows the natural products in the herbs to be obtained without leaving chemical residues behind in the preparation.

Surprisingly, in addition to the anti-inflammatory action disclosed in U.S. Pat. No. 6,387,416, we have found that using the inventive compositions and methods produce COX-2 inhibition and anti-neoplastic activity in prostatic intraepithelial neoplasia cell lines. We also expect that the inventive methods induce apoptosis and inhibit cell growth in prostatic intraepithelial neoplasia cells which have deactivated apoptotic pathways.

The inventive subject matter is based on the discovery that a combination of certain herbs properly extracted and blended in appropriate proportions can used in treating prostatic intraepithelial neoplasia. Thus, the present inventive subject matter relates to a method for treating prostatic intraepithelial neoplasia in a subject, comprising the step of administering an effective amount of a composition to said subject to treat or prevent said prostatic intraepithelial neoplasia, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

In one aspect, said composition is administered orally.

In another preferred embodiment, the orally administered composition is in the form of one or more capsules, one or more tablets, or one or more pills In another aspect, the composition comprises:
(A) from about 4.5% to about 7.5%, and more preferably from about 5.5% to about 6.5%, by weight of the hydroalcoholic extract of ginger;
(B) from about 5.5% to about 8.5%, and more preferably from about 6% to about 8%, by weight of the supercritical extract of ginger;
(C) from about 1.0% to about 1.5%, and more preferably from about 1.2% to about 1.4%, by weight of the supercritical extract of turmeric;
(D) from about 10.0% to about 16.0%, and more preferably from about 11.5% to about 14.5%, by weight of the supercritical extract of rosemary;
(E) from about 4.0% to about 6.0%, and more preferably from about 4.5% to about 5.5%, by weight of the supercritical extract of oregano;
(F) from about 10.0% to about 16.0%, and more preferably from about 11.5% to about 14.5%, by weight of the hydroalcoholic extract of turmeric;
(G) from about 5.5% to about 8.0%, and more preferably from about 6.0% to about 7.0%, by weight of the hydroalcoholic extract of rosemary;
(H) from about 10.0% to about 16.0%, and more preferably from about 11.5% to about 14.5%, by weight of the hydroalcoholic extract of holy basil;
(I) from about 10.0% to about 16.0%, and more preferably from about 11.5% to about 14.5%, by weight of the hydroalcoholic extract of green tea;
(J) from about 8.0% to about 12.0%, and more preferably from about 9.0% to about 11.0%, by weight of the hydroalcoholic extract of huzhang;
(K) from about 4.0% to about 6.0%, and more preferably from about 4.5% to about 5.5%, by weight of the hydroalcoholic extract of Chinese goldthread;
(L) from about 4.0% to about 6.0%, and more preferably from about 4.5% to about 5.5%, by weight of the hydroalcoholic extract of barberry; and
(M) from about 2.0% to about 3.0%, and more preferably from about 2.25% to about 2.75%, by weight of the hydroalcoholic extract of *Scutellaria baicalensis*.

The hydroalcoholic extract of ginger used in the present invention is preferably prepared as follows. The ginger rhizome, which is preferably cryogenically ground to preserve heat sensitive components, is subjected to supercritical extraction to obtain: (i) an oil extract, referred to herein as "the supercritical extract" of ginger, containing delicate lipophilic components, and (ii) an oil-free residue. The oil-free residue is then extracted in a water/alcohol, preferably water/ethanol, mixture composed of 60–80 parts alcohol and 40–20 parts water. The alcohol/water liquid is then evaporated off, leaving a powdered extract residue, referred to herein as "the hydroalcoholic extract" of ginger.

In a preferred aspect, the weight ratio of the supercritical extract of ginger to the hydroalcoholic extract of ginger is from about 0.9:1 to about 1.4:1.

The supercritical extracts of ginger, rosemary, turmeric and oregano used in the present invention can be prepared according to known supercritical extraction methods, such as disclosed, e.g., in E. Stahl, K. W. Quirin, D. Gerard, Dense Gases for Extraction and Refining, Springer Verlag 4 1988, which is hereby incorporated by reference herein.

The hydroalcoholic extracts of rosemary, turmeric, holy basil, huzhang, Chinese goldthread, barberry, and *Scutellaria baicalensis* used in the present invention can be prepared according to conventional hydroalcoholic extraction techniques. For example, the hydroalcoholic extracts can be prepared by extracting the plant portion in a water/alcohol, preferably water/ethanol, mixture preferably composed of 60–80 parts alcohol and 40–20 parts water, and then evaporating off the water/alcohol liquid, leaving a powdered extract residue referred to herein as "the hydroalcoholic extract". The hydroalcoholic extract of green tea used in the present invention is prepared by extracting the plant portion in a water/alcohol, preferably water/ethanol, mixture, and then evaporating off the water/alcohol liquid mixture at a temperature $\leq 80°$ C., preferably by utilizing a spray-drying technique, leaving a powdered extract residue.

In yet another aspect, the weight ratio of the hydroalcoholic extract of turmeric to the supercritical extract of turmeric is from about 8:1 to about 12:1.

In an alternate aspect, the weight ratio of the supercritical extract of rosemary to the hydroalcoholic extract of rosemary is from about 1.6:1 to about 2.4:1.

In a still further aspect, the hydroalcoholic extract of ginger comprises from about 2.4% to about 3.6%, more preferably from about 2.7% to about 3.3%, and most preferably about 3.0%, by weight of pungent compounds.

In another aspect, the supercritical extract of ginger comprises from about 24% to about 36%, more preferably from about 27% to about 33%, and most preferably about 30%, by weight of pungent compounds; and from about 6.4% to about 9.6%, more preferably from about 7.2% to about 8.8%, and most preferably about 8%, by weight of zingiberene.

In a further aspect, the supercritical extract of turmeric comprises from about 36% to about 54%, more preferably from about 40.5% to about 49.5%, and most preferably about 45%, by weight of turmerones.

In another aspect, the supercritical extract of rosemary comprises from about 18.4% to about 27.6%, more preferably from about 20.7% to about 25.3%, and most preferably about 23%, by weight of total phenolic antioxidants.

In yet another aspect, the supercritical extract of oregano comprises from about 0.64% to about 0.96%, more preferably from about 0.72% to about 0.88%, and most preferably about 0.8%, by weight of total phenolic antioxidants.

In a still further aspect, the hydroalcoholic extract of turmeric comprises from about 5.6% to about 8.4%, more preferably from about 6.3% to about 7.7%, and most preferably about 7%, by weight of curcumin.

In another aspect, the hydroalcoholic extract of rosemary comprises from about 18.4% to about 27.6%, more preferably from about 20.7% to about 25.3%, and most preferably about 23%, by weight of total phenolic antioxidants.

In a further embodiment, the hydroalcoholic extract of holy basil comprises from about 1.6% to about 2.4%, more preferably from about 1.8% to about 2.2%, and most preferably about 2%, by weight of ursolic acid.

In a further aspect, the hydroalcoholic extract of green tea comprises from about 36% to about 54%, more preferably from about 40.5% to about 49.5%, and most preferably about 45%, by weight of polyphenols.

In another aspect, the hydroalcoholic extract of huzhang comprises from about 6.4% to about 9.6%, more preferably from about 7.2% to about 8.8%, and most preferably about 8%, by weight of resveratrol.

In another embodiment, the hydroalcoholic extract of Chinese goldthread comprises from about 4.8% to about 7.2%, more preferably from about 5.4% to about 6.6%, and most preferably about 6%, by weight of berberine.

In a further aspect, the hydroalcoholic extract of barberry comprises from about 4.8% to about 7.2%, more preferably from about 5.4% to about 6.6%, and most preferably about 6%, by weight of berberine.

In an alternate aspect, said composition comprises:
(A) from about 4.5% to about 7.5% by weight of the hydroalcoholic extract of ginger, wherein the extract comprises from about 2.4% to about 3.6% by weight of pungent compounds;
(B) from about 5.5% to about 8.5% by weight of the supercritical extract of ginger, wherein the extract comprises from about 24% to about 36% by weight of pungent compounds and from about 6.4% to about 9.6% by weight of zingiberene;
(C) from about 1.0% to about 1.5% by weight of the supercritical extract of turmeric, wherein the extract comprises from about 36% to about 54% by weight of turmerones;
(D) from about 10.0% to about 16.0% by weight of the supercritical extract of rosemary, wherein the extract comprises from about 18.4% to about 27.6% by weight of total phenolic antioxidants;
(E) from about 4.0% to about 6.0% by weight of the supercritical extract of oregano, wherein the extract comprises from about 0.64% to about 0.96% by weight of total phenolic antioxidants;
(F) from about 10.0% to about 16.0% by weight of the hydroalcoholic extract of turmeric, wherein the extract comprises from about 5.6% to about 8.4% by weight of curcumin;
(G) from about 5.5% to about 8.0% by weight of the hydroalcoholic extract of rosemary, wherein the extract comprises from about 18.4% to about 27.6% by weight of total phenolic antioxidants;
(H) from about 10.0% to about 16.0% by weight of the hydroalcoholic extract of holy basil, wherein the extract comprises from about 1.6% to about 2.4% by weight of ursolic acid;
(I) from about 10.0% to about 16.0% by weight of the hydroalcoholic extract of green tea, wherein the extract comprises from about 36% to about 54% by weight of polyphenols;

(J) from about 8.0% to about 12.0% by weight of the hydroalcoholic extract of huzhang, wherein the extract comprises from about 6.4% to about 9.6% by weight of resveratrol;

(K) from about 4.0% to about 6.0% by weight of the hydroalcoholic extract of Chinese goldthread, wherein the extract from about 4.8% to about 7.2% by weight of berberine;

(L) from about 4.0% to about 6.0% by weight of the hydroalcoholic extract of barberry, wherein the extract from about 4.8% to about 7.2% by weight of berberine; and (M) from about 2.0% to about 3.0% by weight of the hydroalcoholic extract of *Scutellaria baicalensis;* and wherein said composition further comprises:

(i) the supercritical extract of ginger and the hydroalcoholic extract of ginger at a weight ratio of from about 0.9 to about 1.4 parts of supercritical extract per 1 part of post-supercritical hydroalcoholic extract;

(ii) the hydroalcoholic extract of turmeric and the supercritical extract of turmeric at a weight ratio of from about 8 to about 12 parts of hydroalcoholic extract per 1 part of supercritical extract; and (iii) the supercritical extract of rosemary and the hydroalcoholic extract of rosemary at a weight ratio of from about 1.6 to about 2.4 parts of supercritical extract per 1 part of hydroalcoholic extract.

In a preferred embodiment, the composition is administered in a daily dosage of at least about 700 mg.

In another aspect, the composition is administered on a daily basis for at least 4 weeks.

In a still further embodiment of the present inventive subject matter, the method for precancerous cellular proliferations within prostatic ducts, ductiles and acini in a subject, comprises the step of administering an effective amount of a composition to said subject to treat or prevent said precancerous cellular proliferations, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis,* rosemary, green tea, huzhang, Chinese goldthread, and barberry.

A benefit provided by the inventive compositions is the utilization of supercritical extraction, an innovative technology for extracting herbs at low temperature without the use of industrial chemical solvents. Such extraction process allows for the highest potency of active compounds in the extracts, as much as 250 times the potency of the original fresh plant material.

Set forth in Table I is a preferred embodiment of the orally administered composition, excluding inactive ingredients, as used in the inventive methods. The amounts recited in Table I represent the preferred dosage of the ingredients listed.

TABLE I

| Herb | Type Of Extract | Plant Part | Amount (mg) |
| --- | --- | --- | --- |
| Rosemary | supercritical | leaf | 100 |
| Rosemary | hydroalcoholic (23% TPA - 34.5 mg) | leaf | 50 |
| Turmeric | supercritical (45% turmerones - 4.5 mg) | rhizome | 10 |
| Turmeric | hydroalcoholic (7% curcumin - 7 mg) | rhizome | 100 |
| Ginger | supercritical (30% pungent compounds - 16.2 mg 8% zingiberene - 4.3 mg) | rhizome | 54 |
| Ginger | hydroalcoholic (3% pungent compounds - 1.4 mg) | rhizome | 46 |
| Holy basil | hydroalcoholic (2% ursolic acid - 2 mg) | leaf | 100 |
| Green tea | hydroalcoholic (45% polyphenols - 45 mg) | leaf | 100 |
| Huzhang | hydroalcoholic (8% resveratrol - 6.4 mg) | root & rhizome | 80 |
| Chinese Goldthread | hydroalcoholic (6% berberine - 2.4 mg) | root | 40 |
| Barberry | hydroalcoholic (6% berberine - 2.4 mg) | root | 40 |
| Oregano | supercritical (0.8% TPA - 0.32 mg) | leaf | 40 |
| *Scutellaria baicalensis* | hydroalcoholic (5:1) | root | 20 |

Preferably, the composition set forth in Table I also includes extra virgin olive oil and yellow beeswax.

The inventive methods use a therapeutically effective amount of the active compositions indicated above. This effective amount will generally comprise from about 0.1 mg to about 100 mg of the active agent per kilogram of patient body weight per day. This effective amount can vary depending upon the physical status of the patient and other factors well known in the art. Moreover, it will be understood that this dosage of active agent can be administered in a single or multiple dosage units to provide the desired therapeutic effect. If desired, other therapeutic agents can be employed in conjunction with those provided by the present inventive subject matter.

The inventive methods use compositions which are preferably delivered to the patient by means of a pharmaceutically acceptable carrier. Such carriers are well known in the art and generally will be in either solid or liquid form. Solid form pharmaceutical preparations which may be prepared according to the present inventive subject matter include powders, tablets, dispersible granules, capsules, and cachets. In general, solid form preparations will comprise from about 5% to about 90% by weight of the active agent.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating materials as a carrier which may provide a capsule in which the active component (with or without other carriers) is surrounded by carrier, which is thus in association with it. Similarly, cachets are included. Tablets, powders, cachets, and capsules can be used as solid dosage forms suitable for oral administration. If desired for reasons of convenience or patient acceptance, pharmaceutical tablets prepared according to the inventive subject matter may be provided in chewable form, using techniques well known in the art.

Also contemplated as suitable carriers are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. Naturally, the liquid utilized will be chosen with regard to the route of administration. For example, liquid preparations containing large amounts of ethanol are not suitable for parenteral use.

The pharmaceutical preparation may also be in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The pharmaceutical preparations of the inventive subject matter may include one or more preservatives well known in the art, such as benzoic acid, sorbic acid, methylparaben, propylparaben and ethylenediaminetetraacetic acid (EDTA). Preservatives are generally present in amounts up to about 1% and preferably from about 0.05 to about 0.5% by weight of the pharmaceutical composition.

Useful buffers for purposes of the inventive subject matter include citric acid-sodium citrate, phosphoric acid-sodium phosphate, and acetic acid-sodium acetate in amounts up to about 1% and preferably from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the pharmaceutical composition.

Sweeteners which may be employed include those sweeteners, both natural and artificial, well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition.

Flavorants which may be employed in the pharmaceutical products of the inventive subject matter include both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the pharmaceutical composition.

Colorants useful in the present inventive subject matter include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D.&C. dyes and the like. Such dyes are generally present in amounts up to about 0.25% and preferably from about 0.05% to about 0.2% by weight of the pharmaceutical composition. A full recitation of all F.D.&C. and D.&C. dyes and their corresponding chemical structures may be found in the Kirk-Othmer Encyclopedia of Chemical Technology, in Volume 5, at pages 857–884, which text is accordingly incorporated herein by reference.

Useful solubilizers include alcohol, propylene glycol, polyethylene glycol and the like and may be used to solubilize the flavors. Solubilizing agents are generally present in amounts up to about 10%; preferably from about 2% to about 5% by weight of the pharmaceutical composition.

Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

It is not expected that the inventive methods use compositions which will display significant adverse interactions with other synthetic or naturally occurring substances. Thus, a compound of the present inventive subject matter may be administered in combination with other compounds and compositions useful for treating prostatic intraepithelial neoplasia. In particular the inventive methods use compositions which may be administered in combination with other inventive compositions, other anti-neoplastic substances, and the like.

The optimal pharmaceutical formulations will be determined by one skilled in the art depending upon considerations such as the route of administration and desired dosage. See, for example, "Remington's Pharmaceutical Sciences", 18th ed. (1990, Mack Publishing Co., Easton, Pa. 18042), pp. 1435–1712, which is hereby incorporated by reference in its entirety. Such formulations may influence the physical state, stability, rate of in vivo release, and rate of in vivo clearance of the present therapeutic agents of the inventive subject matter.

Route(s) of Administration

The compounds and compositions are preferably administered orally in the form of capsules, tablets, aqueous suspensions, or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening, flavoring, coloring agents, or combinations thereof. Delivery in an enterically coated tablet, caplet, or capsule, to further enhance stability and provide release in the intestinal tract to improve absorption, is the best mode of administration currently contemplated.

Dosage

Dosage levels on the order of about 0.001 mg to about 100 mg per kilogram body weight of the active ingredient compounds or compositions are useful in the treatment of the above conditions, with preferred levels ranging from 200 mg per day to 1600 mg per day. The compounds and compositions of the present inventive subject matter may usually be given in two or three doses daily. Starting with a low dose (200–300 mg) twice daily and slowly working up to higher doses if needed is a preferred strategy. The amount of active ingredient that may be combined with the carrier materials to produce a single dosage form will vary depending upon the host treated and the particular mode of administration.

It is understood, however, that a specific dose level for any particular patient will depend upon a variety of factors, including the activity of the specific compound employed; the age, body weight, general health, sex and diet of the patient; the time of administration; the rate of excretion; drug combination; the severity of the particular disorder being treated; and the form of administration. One of ordinary skill in the art would appreciate the variability of such factors and would be able to establish specific dose levels using no more than routine experimentation.

EXAMPLES

The following examples are illustrative of the present inventive subject matter and are not intended to be limitations thereon. Unless otherwise indicated, all percentages are based upon 100% by weight of the final composition.

Example 1

Preparation of the Inventive Compositions

The inventive compositions are prepared by methods known in the art, and disclosed in Applicants' U.S. Pat. No. 6,387,416. The contents of U.S. Pat. No. 6,387,416 are hereby incorporated by reference in their entirety. The preparation of the component elements of the inventive compositions is summarized as follows:

The hydroalcoholic extract of ginger used in the inventive compositions is preferably prepared as follows. The ginger rhizome, which is preferably cryogenically ground to preserve heat sensitive components, is subjected to supercritical extraction to obtain: (i) an oil extract, referred to herein as "the supercritical extract" of ginger, containing delicate lipophilic components, and (ii) an oil-free-residue. The oil-free residue is then extracted in a water/alcohol, preferably water/ethanol, mixture composed of 60–80 parts alcohol and 40–20 parts water. The alcohol/water liquid is then evaporated off, leaving a powdered extract residue, referred to herein as "the hydroalcoholic extract" of ginger.

The composition of this invention will preferably contain the supercritical extract and the hydroalcoholic extract of ginger at a weight ratio of preferably from about 0.9 to about 1.4 parts, more preferably from about 1.1 to about 1.3 parts, most preferably about 1.17 parts, of supercritical extract per 1 part post-supercritical hydroalcoholic extract.

The supercritical extracts of ginger, rosemary, turmeric and oregano used in the inventive compositions can be prepared according to known supercritical extraction methods, such as disclosed, e.g., in E. Stahl, K. W. Quirin, D. Gerard, Dense Gases for Extraction and Refining, Springer Verlag 4 1988, which is hereby incorporated by reference herein.

The hydroalcoholic extracts of rosemary, turmeric, holy basil, huzhang, Chinese goldthread, barberry and *Scutellaria baicalensis* used in the inventive compositions can be prepared according to conventional hydroalcoholic extraction techniques. For example, the hydroalcoholic extracts can be prepared by extracting the plant portion in a water/alcohol (preferably water/ethanol) mixture (preferably composed of 60–80 parts alcohol and 40–20 parts water), and then evaporating off the water/alcohol liquid, leaving a powdered extract residue (referred to herein as "the hydroalcoholic extract"). The hydroalcoholic extract of green tea used in the present invention is prepared by extracting the plant portion in a water/alcohol, preferably water/ethanol, mixture, and then evaporating off the water/alcohol liquid mixture at a temperature $\leq 80°$ C., preferably by utilizing a spray-drying technique, leaving a powdered extract residue.

In the composition of this invention, the hydroalcoholic extract of turmeric and the supercritical extract of turmeric will preferably be present at a weight ratio of preferably from about 8 to about 12 parts, more preferably from about 9 parts to about 11 parts, most preferably about 10 parts, of hydroalcoholic extract per 1 part of supercritical extract.

The composition of this invention will preferably contain the supercritical extract of rosemary and the hydroalcoholic extract of rosemary at a weight ratio of preferably from about 1.6 to about 2.4 parts, more preferably from about 1.8 to about 2.2 parts, most preferably about 2.0 parts, of supercritical extract per 1 part of hydroalcoholic extract.

The hydroalcoholic extract of ginger used in the inventive compositions will preferably contain from about 2.4% to about 3.6%, more preferably from about 2.7% to about 3.3%, most preferably about 3.0%, by weight of pungent compounds (e.g., shogaol).

The supercritical extract of ginger used in the inventive compositions will contain preferably from about 24% to about 36%, more preferably from about 27% to about 33%, most preferably about 30%, by weight of pungent compounds (e.g., shogaol) and preferably from about 6.4% to about 9.6%, more preferably from about 7.2% to about 8.8%, most preferably about 8%, by weight of zingiberene.

The supercritical extract of turmeric used in the inventive compositions will contain preferably from about 36% to about 54%, more preferably from about 40.5% to about 49.5%, most preferably about 45%, by weight of turmerones.

The supercritical extract of rosemary used in the inventive compositions will contain preferably from about 18.4% to about 27.6%, more preferably from about 20.7% to about 25.3%, most preferably about 23%, by weight of total phenolic antioxidants ("TPA").

The supercritical extract of oregano used in the inventive compositions will contain preferably from about 0.64% to about 0.96%, more preferably from about 0.72% to about 0.88%, most preferably about 0.8%, by weight of TPA.

The hydroalcoholic extract of turmeric used in the inventive compositions will contain preferably from about 5.6% to about 8.4%, more preferably from about 6.3% to about 7.7%, most preferably about 7%, by weight of curcumin.

The hydroalcoholic extract of rosemary used in the inventive compositions will contain preferably from about 18.4% to about 27.6%, more preferably from about 20.7% to about 25.3%, most preferably about 23%, by weight of TPA.

The hydroalcoholic extract of holy basil used in the inventive compositions will contain preferably from about 1.6% to about 2.4%, more preferably from about 1.8% to about 2.2%, most preferably about 2%, by weight of ursolic acid.

The hydroalcoholic extract of green tea used in the inventive compositions will contain preferably from about 36% to about 54%, more preferably from about 40.5% to about 49.5%, most preferably about 45%, by weight of polyphenols.

The hydroalcoholic extract of huzhang used in the inventive compositions will contain preferably from about 6.4% to about 9.6%, more preferably from about 7.2% to about 8.8%, most preferably about 8%, by weight of resveratrol.

The hydroalcoholic extract of Chinese goldthread used in the inventive compositions will contain preferably from about 4.8% to about 7.2%, more preferably from about 5.4% to about 6.6%, most preferably about 6%, by weight of berberine.

The hydroalcoholic extract of barberry used in the inventive compositions will contain preferably from about 4.8% to about 7.2%, more preferably from about 5.4% to about 6.6%, most preferably about 6%, by weight of berberine.

Example 2

Effect of the Inventive Compositions on Pre-malignant Prostatic Intraepithelial Neoplasia A patient presents for treatment of a pre-malignant intraepithelial neoplasia of the prostate. An inventive composition is administered to said patient over a course of treatment lasting for several weeks, resulting in no significant side effects. The patient experiences a reversal in the growth of pre-malignant neoplastic cells and death of existing pre-malignant neoplastic cells, resulting in the prostatic intraepithelial neoplasia becoming undetectable. With continuing treatment, the patient continues to exhibit no secondary symptoms of prostatic intraepithelial neoplasia, no long term side effects of the treatment, and does not develop prostate cancer.

The inventive subject matter being thus described, it will be obvious that the same may be modified or varied in many ways. Such modifications and variations are not to be regarded as a departure from the spirit and scope of the inventive subject matter and all such modifications and variations are intended to be included within the scope of the following claims.

We claim:

1. A method for treating prostatic intraepithelial neoplasia in a subject, comprising the step of administering an effective amount of a composition to said subject to treat said prostatic intraepithelial neoplasia, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

2. The method of claim 1, wherein said composition is administered orally.

3. The method of claim 2, wherein the orally administered composition is in the form of one or more capsules, one or more tablets, or one or more pills.

4. The method of claim 1, wherein the composition comprises:
   (A) from about 4.5% to about 7.5% by weight of the hydroalcoholic extract of ginger;
   (B) from about 5.5% to about 8.5% by weight of the supercritical extract of ginger;
   (C) from about 1.0% to about 1.5% by weight of the supercritical extract of turmeric;
   (D) from about 10.0% to about 16.0% by weight of the supercritical extract of rosemary;
   (E) from about 4.0% to about 6.0% by weight of the supercritical extract of oregano;
   (F) from about 10.0% to about 16.0% by weight of the hydroalcoholic extract of turmeric;
   (G) from about 5.5% to about 8.0% by weight of the hydroalcoholic extract of rosemary;
   (H) from about 10.0% to about 16.0% by weight of the hydroalcoholic extract of holy basil;
   (I) from about 10.0% to about 16.0% by weight of the hydroalcoholic extract of green tea;
   (J) from about 8.0% to about 12.0% by weight of the hydroalcoholic extract of huzhang;
   (K) from about 4.0% to about 6.0% by weight of the hydroalcoholic extract of Chinese goldthread;
   (L) from about 4.0% to about 6.0% by weight of the hydroalcoholic extract of barberry; and
   (M) from about 2.0% to about 3.0% by weight of the hydroalcoholic extract of *Scutellaria baicalensis*.

5. The method of claim 1, wherein the weight ratio of the supercritical extract of ginger to the hydroalcoholic extract of ginger is from about 0.9:1 to about 1.4:1.

6. The method of claim 1, wherein the weight ratio of the hydroalcoholic extract of turmeric to the supercritical extract of turmeric is from about 8:1 to about 12:1.

7. The method of claim 1, wherein the weight ratio of the supercritical extract of rosemary to the hydroalcoholic extract of rosemary is from about 1.6:1 to about 2.4:1.

8. The method of claim 1, wherein the hydroalcoholic extract of ginger comprises from about 2.4% to about 3.6% by weight of pungent compounds.

9. The method of claim 1, wherein the supercritical extract of ginger comprises from about 24% to about 36% by weight of pungent compounds and from about 6.4% to about 9.6% by weight of zingiberene.

10. The method of claim 1, wherein the supercritical extract of turmeric comprises from about 36% to about 54% by weight of turmerones.

11. The method of claim 1, wherein the supercritical extract of rosemary comprises from about 18.4% to about 27.6% by weight of total phenolic antioxidants.

12. The method of claim 1, wherein the supercritical extract of oregano comprises from about 0.64% to about 0.96% by weight of total phenolic antioxidants.

13. The method of claim 1, wherein the hydroalcoholic extract of turmeric comprises from about 5.6% to about 8.4% by weight of curcumin.

14. The method of claim 1, wherein the hydroalcoholic extract of rosemary comprises from about 18.4% to about 27.6% by weight of total phenolic antioxidants.

15. The method of claim 1, wherein the hydroalcoholic extract of holy basil comprises from about 1.6% to about 2.4% by weight of ursolic acid.

16. The method of claim 1, wherein the hydroalcoholic extract of green tea comprises from about 36% to about 54% by weight of polyphenols.

17. The method of claim 1, wherein the hydroalcoholic extract of huzhang comprises from about 6.4% to about 9.6% by weight of resveratrol.

18. The method of claim 1, wherein the hydroalcoholic extract of Chinese goldthread comprises from about 4.8% to about 7.2% by weight of berberine.

19. The method of claim 1, wherein the hydroalcoholic extract of barberry comprises from about 4.8% to about 7.2% by weight of berberine.

20. The method of claim 1, wherein said composition provided in step (a) comprises:
- (A) from about 4.5% to about 7.5% by weight of the hydroalcoholic extract of ginger, wherein the extract comprises from about 2.4% to about 3.6% by weight of pungent compounds;
- (B) from about 5.5% to about 8.5% by weight of the supercritical extract of ginger, wherein the extract comprises from about 24% to about 36% by weight of pungent compounds and from about 6.4% to about 9.6% by weight of zingiberene;
- (C) from about 1.0% to about 1.5% by weight of the supercritical extract of turmeric, wherein the extract comprises from about 36% to about 54% by weight of turmerones;
- (D) from about 10.0% to about 16.0% by weight of the supercritical extract of rosemary, wherein the extract comprises from about 18.4% to about 27.6% by weight of total phenolic antioxidants;
- (E) from about 4.0% to about 6.0% by weight of the supercritical extract of oregano, wherein the extract comprises from about 0.64% to about 0.96% by weight of total phenolic antioxidants;
- (F) from about 10.0% to about 16.0% by weight of the hydroalcoholic extract of turmeric, wherein the extract comprises from about 5.6% to about 8.4% by weight of curcumin;
- (G) from about 5.5% to about 8.0% by weight of the hydroalcoholic extract of rosemary, wherein the extract comprises from about 18.4% to about 27.6% by weight of total phenolic antioxidants;
- (H) from about 10.0% to about 16.0% by weight of the hydroalcoholic extract of holy basil, wherein the extract comprises from about 1.6% to about 2.4% by weight of ursolic acid;
- (I) from about 10.0% to about 16.0% by weight of the hydroalcoholic extract of green tea, wherein the extract comprises from about 36% to about 54% by weight of polyphenols;
- (J) from about 8.0% to about 12.0% by weight of the hydroalcoholic extract of huzhang, wherein the extract comprises from about 6.4% to about 9.6% by weight of resveratrol;
- (K) from about 4.0% to about 6.0% by weight of the hydroalcoholic extract of Chinese goldthread, wherein the extract from about 4.8% to about 7.2% by weight of berberine;
- (L) from about 4.0% to about 6.0% by weight of the hydroalcoholic extract of barberry, wherein the extract from about 4.8% to about 7.2% by weight of berberine; and
- (M) from about 2.0% to about 3.0% by weight of the hydroalcoholic extract of *Scutellaria baicalensis*;

and wherein said composition further comprises:
- (i) the supercritical extract of ginger and the hydroalcoholic extract of ginger at a weight ratio of from about 0.9 to about 1.4 parts of supercritical extract per 1 part of hydroalcoholic extract;
- (ii) the hydroalcoholic extract of turmeric and the supercritical extract of turmeric at a weight ratio of from about 8 to about 12 parts of hydroalcoholic extract per 1 part of supercritical extract; and
- (iii) the supercritical extract of rosemary and the hydroalcoholic extract of rosemary at a weight ratio of from about 1.6 to about 2.4 parts of supercritical extract per 1 part of hydroalcoholic extract.

21. The method of claim 1, said composition is administered in a daily dosage of at least about 700 mg.

22. The method of claim 1, wherein said composition is administered on a daily basis for at least 4 weeks.

23. A method for treating precancerous cellular proliferations within prostatic ducts, ductiles and acini in a subject, comprising the step of administering an effective amount of a composition to said subject to treat said precancerous cellular proliferations, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

24. The method of claim 23, wherein said composition is administered orally.

25. The method of claim 24, wherein the orally administered composition is in the form of one or more capsules, one or more tablets, or one or more pills.

26. The method of claim 23, wherein the composition comprises:
- (A) from about 4.5% to about 7.5% by weight of the hydroalcoholic extract of ginger;
- (B) from about 5.5% to about 8.5% by weight of the supercritical extract of ginger;
- (C) from about 1.0% to about 1.5% by weight of the supercritical extract of turmeric;
- (D) from about 10.0% to about 16.0% by weight of the supercritical extract of rosemary;
- (E) from about 4.0% to about 6.0% by weight of the supercritical extract of oregano;
- (F) from about 10.0% to about 16.0% by weight of the hydroalcoholic extract of turmeric;
- (G) from about 5.5% to about 8.0% by weight of the hydroalcoholic extract of rosemary;
- (H) from about 10.0% to about 16.0% by weight of the hydroalcoholic extract of holy basil;
- (I) from about 10.0% to about 16.0% by weight of the hydroalcoholic extract of green tea;
- (J) from about 8.0% to about 12.0% by weight of the hydroalcoholic extract of huzhang;
- (K) from about 4.0% to about 6.0% by weight of the hydroalcoholic extract of Chinese goldthread;
- (L) from about 4.0% to about 6.0% by weight of the hydroalcoholic extract of barberry; and
- (M) from about 2.0% to about 3.0% by weight of the hydroalcoholic extract of *Scutellaria baicalensis*.

27. The method of claim 23, wherein the weight ratio of the supercritical extract of ginger to the hydroalcoholic extract of ginger is from about 0.9:1 to about 1.4:1.

28. The method of claim 23, wherein the weight ratio of the hydroalcoholic extract of turmeric to the supercritical extract of turmeric is from about 8:1 to about 12:1.

29. The method of claim 23, wherein the weight ratio of the supercritical extract of rosemary to the hydroalcoholic extract of rosemary is from about 1.6:1 to about 2.4:1.

30. The method of claim 23, wherein the post supercritical hydroalcoholic extract of ginger comprises from about 2.4% to about 3.6% by weight of pungent compounds.

31. The method of claim 23, wherein the supercritical extract of ginger comprises from about 24% to about 36% by weight of pungent compounds and from about 6.4% to about 9.6% by weight of zingiberene.

32. The method of claim 23, wherein the supercritical extract of turmeric comprises from about 36% to about 54% by weight of turmerones.

33. The method of claim 23, wherein the supercritical extract of rosemary comprises from about 18.4% to about 27.6% by weight of total phenolic antioxidants.

34. The method of claim 23, wherein the supercritical extract of oregano comprises from about 0.64% to about 0.96% by weight of total phenolic antioxidants.

35. The method of claim 23, wherein the hydroalcoholic extract of turmeric comprises from about 5.6% to about 8.4% by weight of curcumin.

36. The method of claim 23, wherein the hydroalcoholic extract of rosemary comprises from about 18.4% to about 27.6% by weight of total phenolic antioxidants.

37. The method of claim 23, wherein the hydroalcoholic extract of holy basil comprises from about 1.6% to about 2.4% by weight of ursolic acid.

38. The method of claim 23, wherein the hydroalcoholic extract of green tea comprises from about 36% to about 54% by weight of polyphenols.

39. The method of claim 23, wherein the hydroalcoholic extract of huzhang comprises from about 6.4% to about 9.6% by weight of resveratrol.

40. The method of claim 23, wherein the hydroalcoholic extract of Chinese goldthread comprises from about 4.8% to about 7.2% by weight of berberine.

41. The method of claim 23, wherein the hydroalcoholic extract of barberry comprises from about 4.8% to about 7.2% by weight of berberine.

42. The method of claim 23, said composition is administered in a daily dosage of at least about 700 mg.

43. The method of claim 23, wherein said composition is administered on a daily basis for at least 4 weeks.

* * * * *